US00PP36545P2

(12) United States Plant Patent
van Dijk

(10) Patent No.: US PP36,545 P2
(45) Date of Patent: Mar. 11, 2025

(54) ***ANTHURIUM* PLANT NAMED 'AN2736215'**

(50) Latin Name: *Anthurium andreanum*
Varietal Denomination: AN2736215

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/610,216

(22) Filed: Mar. 19, 2024

(51) Int. Cl.
*A01H 5/02* (2018.01)
*A01H 6/10* (2018.01)

(52) U.S. Cl.
USPC ..... Plt./369
CPC ..... *A01H 6/10* (2018.05)

(58) Field of Classification Search
USPC ..... Plt./369
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Anthurium* plant named 'AN2736215', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and erect scapes; broadly cordate red-colored spathes and red-colored spadices; and durable spathes that impart good inflorescence longevity.

2 Drawing Sheets

Figure 1:
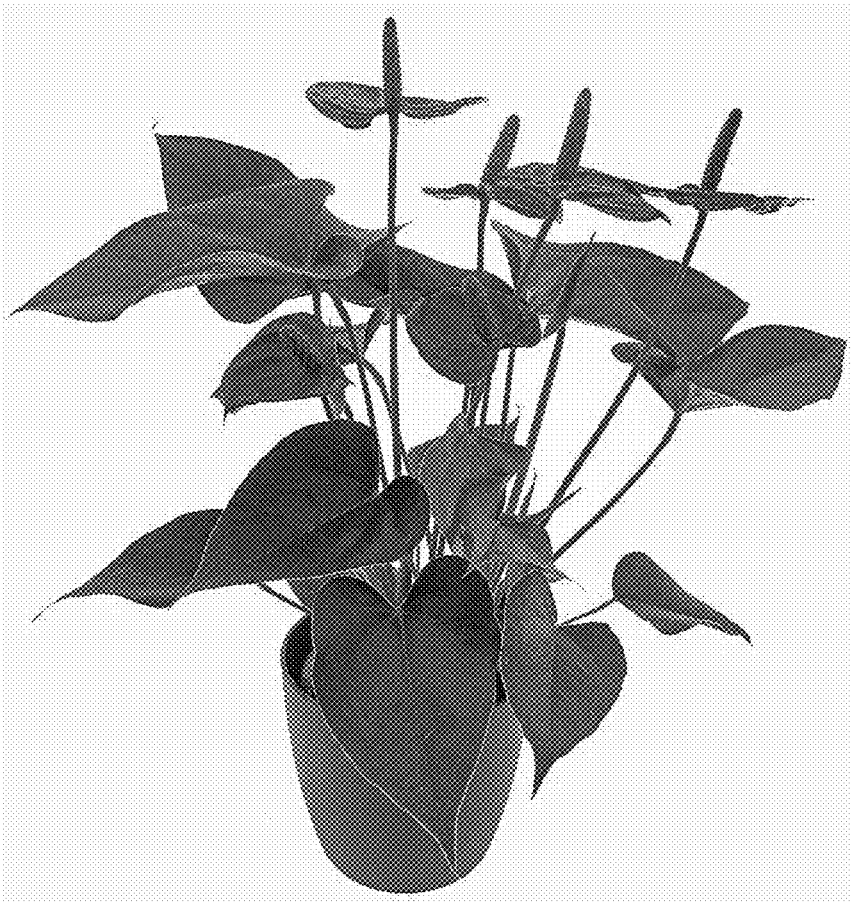

Botanical designation: *Anthurium andreanum.*
Cultivar denomination: 'AN2736215'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B. V. of Bleiswijk, The Netherlands on Nov. 22, 2022, application number 2022/2622. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Anthurium* plant, botanically known as *Anthurium andreanum* and hereinafter referred to by the name 'AN2736215'.

The new *Anthurium* plant is a product of a controlled breeding program conducted by the Inventor in Bleiswijk, The Netherlands. The objective of the breeding program is to create new freely-clumping *Anthurium* plants with attractive red-colored, durable and glossy spathes.

The new *Anthurium* plant originated from a cross-pollination made by the Inventor in January 2013 in Bleiswijk, The Netherlands of *Anthurium andreanum* 'Anthfanxol', disclosed in U.S. Plant Pat. No. 31,489, as the female, or seed, parent with a proprietary selection of *Anthurium andreanum* identified as code number 05-008641-0001, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in April 2015.

Asexual reproduction of the new *Anthurium* plant by in vitro meristem propagation in a controlled environment in Bleiswijk, The Netherlands since December 2016 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2736215'. These characteristics in combination distinguish 'AN2736215' as a new and distinct *Anthurium* plant:

1. Upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and erect scapes.

6. Broadly cordate red-colored spathes and red-colored spadices.
7. Durable spathes that impart good inflorescence longevity.

Plants of the new *Anthurium* differ primarily from plants of the female parent, 'Anthfanxol', in the following characteristics:

1. Leaves of plants of the new *Anthurium* are narrowly cordate in shape whereas leaves of plants of 'Anthfanxol' are ovate in shape.
2. Spadices of plants of the new *Anthurium* are not as tapering as spadices of plants of 'Anthfanxol'.
3. Scapes of plants of the new *Anthurium* are more strongly colored with anthocyanin than scapes of plants of 'Anthfanxol'.

Plants of the new *Anthurium* differ primarily from plants of the male parent selection in the following characteristics:

1. Spathes of plants of the new *Anthurium* are not as rugose as spathes of plants of the male parent selection.
2. Spadices of plants of the new *Anthurium* are red in color whereas spadices of plants of the male parent selection are white and yellow in color.

Plants of the new *Anthurium* can also be compared to plants of *Anthurium andreanum* 'AN2922932', disclosed in U.S. Plant Pat. No. 34,632. In side-by-side comparisons, plants of the new *Anthurium* differ primarily from plants of 'AN2922932' in the following characteristics:

1. Spathes of plants of the new *Anthurium* are not as concave as spathes of plants of 'AN2922932'.
2. Spadices of plants of the new *Anthurium* are not as tapering as spadices of plants of 'AN2922932'.
3. Scapes of plants of the new *Anthurium* are more strongly colored with anthocyanin than scapes of plants of 'AN2922932'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2736215' grown in a container.

Figure 2:
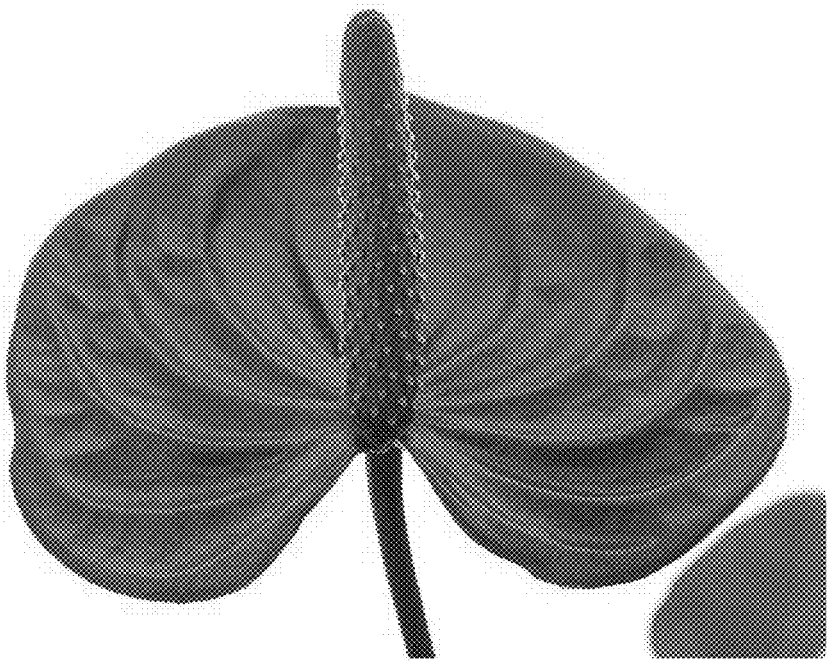

The photograph on the second sheet (FIG. 2) is a close-up view of a typical inflorescence of 'AN2736215'.

DETAILED BOTANICAL DESCRIPTION

The aforementioned photographs and following observations and measurements describe plants grown in 14-cm containers in Bleiswijk, The Netherlands during the autumn in a glass-covered greenhouse. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were eleven months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2736215'.

Parentage:

*Female, or seed, parent.*—*Anthurium andreanum* 'Anthfanxol', disclosed in U.S. Plant Pat. No. 31,489.

*Male, or pollen, parent.*—Proprietary selection of *Anthurium andreanum* identified as code number 05-008641-0001, not patented.

Propagation:

*Type.*—By in vitro meristem propagation.

*Time to initiate roots, summer and winter.*—About two weeks at temperatures about 19° C. to 22.5° C.

*Time to produce a rooted young plant, summer and winter.*—About six to eight weeks at temperatures about 19° C. to 22.5° C.

*Root description.*—Medium in thickness, fibrous; typically creamy white tinged with pink in color, actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly spreading and uniform plant habit; overall shape, broadly ovate to close to globular.

*Growth habit.*—Freely clumping habit with about six clumps per plant imparting a bushy and dense appearance; moderately vigorous growth habit and moderate growth rate.

*Plant height, from soil level to top of leaf plane.*—About 23.5 cm.

*Plant height, from soil level to top of inflorescences.*—About 32.3 cm.

*Plant diameter or spread.*—About 44 cm.

Leaf description:

*Arrangement.*—Alternate; simple; about four leaves per clump.

*Length.*—About 17.1 cm.

*Width.*—About 9.9 cm.

*Shape.*—Narrowly cordate.

*Apex.*—Apiculate with mucronate tip.

*Base.*—Cordate.

*Margin.*—Entire; moderately and coarsely undulate.

*Texture and luster, upper and lower surfaces.*—Smooth, glabrous; moderately leathery; glossy.

*Venation pattern.*—Pinnate.

*Color.*—Developing leaves, upper surface: Slightly darker than 144A. Developing leaves, lower surface: Close to 144A. Fully expanded leaves, upper surface: Darker than a blend of NN137A and 147A; venation, close to 143B. Fully expanded leaves, lower surface: Close to a blend of 146A and 146B; venation, close to 151A with small basal blotch, close to 173B.

*Petioles.*—Length: About 16.6 cm. Diameter: Distally, about 3 mm; proximally, about 4 mm. Strength: Strong. Texture and luster, upper and lower surfaces: Smooth, glabrous; slightly glossy. Color, upper surface: Close to 144A. Color, lower surface: Close to 144A to 144B. Geniculum length: About 1.8 cm. Geniculum diameter: About 4 mm. Geniculum texture and luster, upper and lower surfaces: Smooth, glabrous; slightly glossy. Geniculum color, upper surface: Close to 152B and 152C. Geniculum color, lower surface: Close to 144B. Wing length: About 1.7 cm. Wing diameter: About 5 mm. Wing color: Close to 144B; towards the margins, close to 145A.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting.

*Inflorescence longevity*.—Spathes maintain good substance for about two months on the plant; inflorescences persistent.

*Fragrance*.—None detected.

*Spathes*.—Length: About 8.6 cm. Width: About 8.2 cm. Shape: Broadly cordate; slightly concave. Apex: Abruptly acute. Base: Cordate to reniform. Margin: Entire; coarsely undulate. Aspect: At about 80° from the scape axis. Texture and luster, upper and lower surfaces: Smooth, glabrous; moderately leathery; glossy. Color: When developing, front surface: Close to 45B. When developing, rear surface: Close to 47C; towards the margins and base, close to 46C. Fully developed, front surface: Close to 45B; with subsequent development, color becoming closer to 45B and tinged towards the base with close to 146A and 146B with venation, close to a blend of N186C and N200A. Fully developed, rear surface: Close to 46B and 46C; with subsequent development, color becoming closer to 46C and 46D and towards the base and venation, close to 146C.

*Spadices*.—Length: About 4.8 cm. Diameter: About 1.1 cm. Shape: Columnar, slightly tapering towards the apex; apex, obtuse; base, obtuse; in cross-section, rounded. Aspect: About 75° From the spathe axis and about 10° From the scape axis. Color: Immature: Close to 47A and distally, close to a blend of 42A and 44A. Mature: Close to 184B. Flowers: Type: Hermaphroditic. Quantity per spadix: Numerous, about 120. Height: Less than 0.5 mm. Diameter: About 2 mm. Shape: Roughly square. Anther color: Close to 184B. Pollen amount: Moderate. Pollen color: Close to N155B. Stigma color: Close to 156B tinged with close to 182D.

*Scape*.—Length: About 24.2 cm. Diameter: About 4 mm. Strength: Strong. Aspect: About 20° From vertical. Color: Close to 152A and distally, close to 172A.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2736215' as herein illustrated and described.

* * * * *